US010856839B2

(12) United States Patent
Raju et al.

(10) Patent No.: US 10,856,839 B2
(45) Date of Patent: Dec. 8, 2020

(54) SCANNING TO IDENTIFY AND DELIMIT STATIONARY FLUID POOLS

(71) Applicant: KONINKLIJKE PHILIPS N.V., Eindhoven (NL)

(72) Inventors: Balasundar Iyyavu Raju, Chester, NY (US); Ajay Anand, Fishkill, NY (US); John Petruzzello, Carmel, NY (US)

(73) Assignee: Koninklijke Philips N.V., Eindhoven (NL)

(*) Notice: Subject to any disclaimer, the term of this patent is extended or adjusted under 35 U.S.C. 154(b) by 800 days.

(21) Appl. No.: 14/770,287

(22) PCT Filed: Feb. 26, 2014

(86) PCT No.: PCT/IB2014/059249
§ 371 (c)(1),
(2) Date: Aug. 25, 2015

(87) PCT Pub. No.: WO2014/136018
PCT Pub. Date: Sep. 12, 2014

(65) Prior Publication Data
US 2016/0000398 A1    Jan. 7, 2016

Related U.S. Application Data

(60) Provisional application No. 61/772,737, filed on Mar. 5, 2013.

(51) Int. Cl.
*A61B 8/08* (2006.01)
*A61B 8/06* (2006.01)
(Continued)

(52) U.S. Cl.
CPC ............ *A61B 8/085* (2013.01); *A61B 8/06* (2013.01); *A61B 8/14* (2013.01); *A61B 8/485* (2013.01);
(Continued)

(58) Field of Classification Search
CPC ............ G01S 15/8988; G01S 7/52042; G01S 15/8981; G01S 7/52022; A61B 8/488;
(Continued)

(56) References Cited

U.S. PATENT DOCUMENTS

| 5,487,387 A | 1/1996 | Trahey |
| 6,117,080 A * | 9/2000 | Schwartz ............ A61B 8/0825 600/443 |

(Continued)

FOREIGN PATENT DOCUMENTS

EP    0882426 A2    12/1998

OTHER PUBLICATIONS

Zagrodsky et al. "Automated Detection of a Blood Pool in Ultrasound Images of Abdominal Trauma." Ultrasound in Med & Biol 33:11 (2007), pp. 1720-1726.*

(Continued)

*Primary Examiner* — Angela M Hoffa (57) ABSTRACT

Dynamically identifying a stationary body of fluid (102) within a test volume by scanning within the volume can entail using a first part of a pulse sequence to acoustically interrogate a region within the volume to detect pre-existing movement (124) and, via a separate acoustic interrogation constituting the second part of the pulse sequence, acoustically interrogating the region to distinguish solid from fluid. The scanning is with both interrogations as a unit, so as to span the volume with the interrogations. The body is identified, dynamically based on an outcome of the interrogations. The scanning may span, for the identifying, a current field of view (116), including normal tissue, within an imaging subject. The procedure, from scanning to identifying, may be performed automatically and without need for user intervention, although the user can optionally change the field of view to further search for stationary fluid.

13 Claims, 7 Drawing Sheets

(51) Int. Cl.
*G01S 7/52* (2006.01)
*G01S 15/89* (2006.01)
*A61B 8/14* (2006.01)
*A61B 8/00* (2006.01)

(52) U.S. Cl.
CPC ............ *A61B 8/488* (2013.01); *A61B 8/5207* (2013.01); *A61B 8/5223* (2013.01); *G01S 7/52022* (2013.01); *G01S 7/52042* (2013.01); *G01S 15/8981* (2013.01); *G01S 15/8988* (2013.01); *A61B 8/4427* (2013.01); *A61B 8/4488* (2013.01); *A61B 8/5246* (2013.01)

(58) Field of Classification Search
CPC ........... A61B 8/06; A61B 8/485; A61B 8/085; A61B 8/5223; A61B 8/14; A61B 8/5207; A61B 8/4488; A61B 8/4427; A61B 8/5246
See application file for complete search history.

(56) References Cited

U.S. PATENT DOCUMENTS

| | | | | |
|---|---|---|---|---|
| 8,727,995 | B2* | 5/2014 | Brunke | A61B 8/12 600/462 |
| 2004/0254439 | A1 | 12/2004 | Fowkes | |
| 2010/0168566 | A1 | 7/2010 | Bercoff | |
| 2012/0065507 | A1* | 3/2012 | Brunke | A61B 8/12 600/442 |
| 2012/0143042 | A1 | 6/2012 | Palmeri | |
| 2016/0000411 | A1* | 1/2016 | Raju | A61B 5/6842 600/443 |
| 2016/0239959 | A1* | 8/2016 | Blackbourne | G06K 9/46 |
| 2017/0273658 | A1* | 9/2017 | Wang | A61B 8/085 |

OTHER PUBLICATIONS

Nightingale, Kathryn R. et al "On the Feasibility of Remote Palpation using Acoustic Radiation Force", The Journal of the Acoustical Society of America, American Institute of Physics for the Acoustical Society of America, vol. 110, No. 1, Jul. 2001, pp. 625-634.

Nightingale, Kathryn R. et al, "The Use of Acoustic Streaming in Breast Lesion Diagnosis: A Clinical Study" Ultrasound in Medicine and Biology, vol. 25, No. 1, Jan. 1999, pp. 75-87.

Booi et al "Characterization of Cysts using Differential Correlation Coefficient Values from Two Dimensional Breast Elastography: Preliminary Study", Ultrasound in Medicine and Biology, vol. 34, No. 1, Jan. 2008, pp. 12-21.

Nightingale, Kathryn R. et al, "Generation and Detection of Acoustic Streaming to Differentiate Between Solid and Cystic Breast Lesions", Ultrasonics Symposium, 1994, pp. 1653-1656.

Nightingale, Kathryn R. et al, "A Novel Ultrasonic Technique for Differentiating Cysts from Solid Lesions: Preliminary Results in the Breast", Ultrasound in Medicine and Biology, vol. 21, No. 6, pp. 745-751. 1995.

Edwards, A. et al "Acoustic Streaming: A new Technique for Assessing Adnexal Cysts", Ultrasound Obstet Gynecol. vol. 22, 2003, pp. 74-78.

Starritt, H.C. et al "An Experimental Investigation of Streaming in Pulsed Diagnostic Ultrasound Beams", Ultrasound in Medicine and Biology, vol. 15, No. 4, 1989, pp. 363-373.

* cited by examiner

SCANNING TO IDENTIFY AND DELIMIT STATIONARY FLUID POOLS

CROSS-REFERENCE TO PRIOR APPLICATIONS

This application is the U.S. National Phase application under 35 U.S.C. § 371 of International Application No. PCT/IB2014/059249, filed on Feb. 26, 2014, which claims the benefit of U.S. Provisional Patent Application No. 61/772,737, filed on Mar. 5, 2013. These applications are hereby incorporated by reference herein.

FIELD OF THE INVENTION

The present invention relates to acoustically scanning a region and, more particularly, to dynamically scanning to detect movement and determine physical structure.

BACKGROUND OF THE INVENTION

According to the Centers for Disease Control and Prevention (CDC), trauma accounts for 42 million emergency department visits and 2 million hospital admissions across the USA every year. In the USA, trauma accounts for 38.4 deaths per 100,000 of population. Trauma is especially a leading cause of death in the young population, and accounts for 30% of all life years lost in the USA (compared to 16% for cancer, and 12% for heart diseases).

Ultrasound is often the first imaging examination of patients with major trauma. Ultrasound is non-invasive and portable and is available at low cost compared to computed tomography (CT) or magnetic resonance imaging (MRI).

The FAST (Focused Assessment with Sonography in Trauma) protocols were developed to streamline the process of quick examinations of a trauma patient in the emergency room (ER) by relatively untrained users. The aim of the FAST examination is to assess blood accumulation in four areas in the abdomen/chest, where under normal conditions blood would not be present. During this examination the patient is placed in the supine position and four standard views are obtained: (a) Right upper quadrant (RUQ) (b) Left upper quadrant (LUQ) (c) Subxiphoid and (d) Suprapubic regions. For instance in the RUQ examination, the user would examine for dark hypoehcogenic areas in the Morisson's pouch, the space between the liver and right kidney, where the hypoehcogenicity would indicate presence of accumulated blood. In the LUQ examination the user would look for free fluid between the diaphragm and spleen, and between spleen and kidney, the presence of which would indicate blood pool secondary to organ damage. Likewise, in the suprapubic examination the user would look for free fluid in the pouch of Douglas.

U.S. Pat. No. 5,487,387 to Trahey et al. (hereinafter "Trahey"), the entire disclosure of which is incorporated herein by reference, discloses ultrasonically testing a pre-identified lesion, in a preliminary procedure, to detect vascular blood flow within the lesion. Then, in the actual ultrasonic testing, Trahey examines the physical structure of the lesion.

SUMMARY OF THE INVENTION

What is proposed herein below is directed to addressing one or more of the above concerns.

The Trahey reference does not relate to handling medical emergencies. Nor does it relate to scanning to identify a stationary body of fluid. Nor does it relate to dynamically applying, as a unit, a combination of movement- and physical-structure-detecting interrogations, region by region, in a scan. Nor does it relate to using a scan to automatically, and without the need for user intervention, identify a stationary body of fluid.

The inventors are unaware of any presently-existing device for quickly and reliably ascertaining presence of an intracorporeal blood pool that can be used in an ER or pre-hospital setting without the need for significant user training.

In accordance with an aspect of the present invention, an acoustic device is configured for dynamically identifying a stationary body of fluid within a test volume by scanning within the volume. In particular, a region within the volume is acoustically interrogated to detect pre-existing movement. A separate acoustic interrogation distinguishes solid from fluid. Both interrogations are scanned, as a unit, so as to span the volume. The body is thereby identified, dynamically based on an outcome of the interrogations.

In another aspect, one of the two interrogations is configured for moving body tissue, and the other of the two involves issuing pulses with respective lengths short enough to avoid imparting motion to body fluid.

In an associated aspect, the interrogator generates, and transmits, a sequence of pulses that includes a first part for the interrogation to detect pre-existing movement and a second part for the interrogation to distinguish solid from fluid.

As a sub-aspect, both parts include respective pulses of the sequence, the pulses of the first part being distinct from the pulses of the second part.

As also a sub-aspect, the sequence consists of the first and second parts, that are issued without the device issuing an acoustic pulse transmission that intervenes between the first and second parts.

In one other sub-aspect, the first part occurs, in the sequence, prior to the second part.

In a further sub-aspect of this, the second part commences a time period after completion of issuance of the first part, the period being less than twice a maximum round-trip time-in-flight, of a most recent pulse of the first part, in imaging an imaging subject in performing the identifying.

In an additional sub-aspect, the region is among a plurality of regions the device is configured for scanning, said interrogator being configured for generating, and transmitting, a plurality of pulse sequences per region. The above-mentioned sequence is among the plurality of pulse sequences. The device is further configured for, based on a measurement derived from the outcome of the interrogations in the scanning, determining a spatial extent of the body.

In a more specific aspect or alternative, the scanning is for utilizing a tracking pulse that precedes, and a tracking pulse that follows, at least two intervening push pulses to track a push-induced total non-spatially-overlapping displacement of body tissue, such that the plurality of pulse sequences of a region comprises the intervening push pulses and both tracking pulses. The measurement is based on a result of the displacement tracking.

In a different sub-aspect, the first part includes a blood flow detection pulse, the second part includes an acoustic-radiation-force-imaging (ARFI) push pulse, amplitude being the only parameter that power-wise distinguishes the detection pulse from the push pulse.

In yet another aspect, the interrogation to detect pre-existing movement is configured for identifying fluid that is already moving just prior to the interrogation to detect pre-existing movement.

In still another aspect, the test volume includes a plurality of regions, the above-mentioned region being among the plurality, the scanning comprising, after performing both interrogations of the region, performing both interrogations of a next region of the volume.

As one further alternative or complementary aspect, the device is configured for acoustically pushing body tissue as part of the interrogating to distinguish and for, in the interrogating to distinguish, acquiring respective sets, of data representative of body tissue, that differ due to the pushing. The device is also configured for dynamically computing a correlation coefficient between a pair of the sets.

In a version of the immediately above aspect, the device is configured for, based on a result of the computing, dynamically determining a spatial extent of the body of fluid.

Optionally, the device is implemented as a medical diagnostic apparatus.

In a particular aspect, the interrogation to distinguish solid from fluid is performable selectively responsive to a result of the interrogation to detect pre-existing movement.

In a specific aspect, the scanning performs, with respect to the above-mentioned region, both interrogations one after another.

As a further specific aspect, the scanning spans, for the identifying, a current field of view, of the device, within an imaging subject.

In one other aspect of option, the interrogations both issue ultrasound.

In one other additional aspect, the interrogating to detect pre-existing movement includes interrogating to detect intracorporeal, naturally occurring fluid motion.

In a complementary or alternative aspect, the distinguishing is based on detecting an imaging-depth-wise staggering, of echo data, over a series of tracking pulses.

As one additional aspect or feature, the identifying includes identifying a spatial extent of the identified body.

In one more specific aspect, the scanning includes scanning normal body tissue for the identifying.

Details of the novel, stationary-pool identifying technology are set forth further below, with the aid of the following drawings, which are not drawn to scale.

DETAILED DESCRIPTION OF EMBODIMENTS

Figure 1:
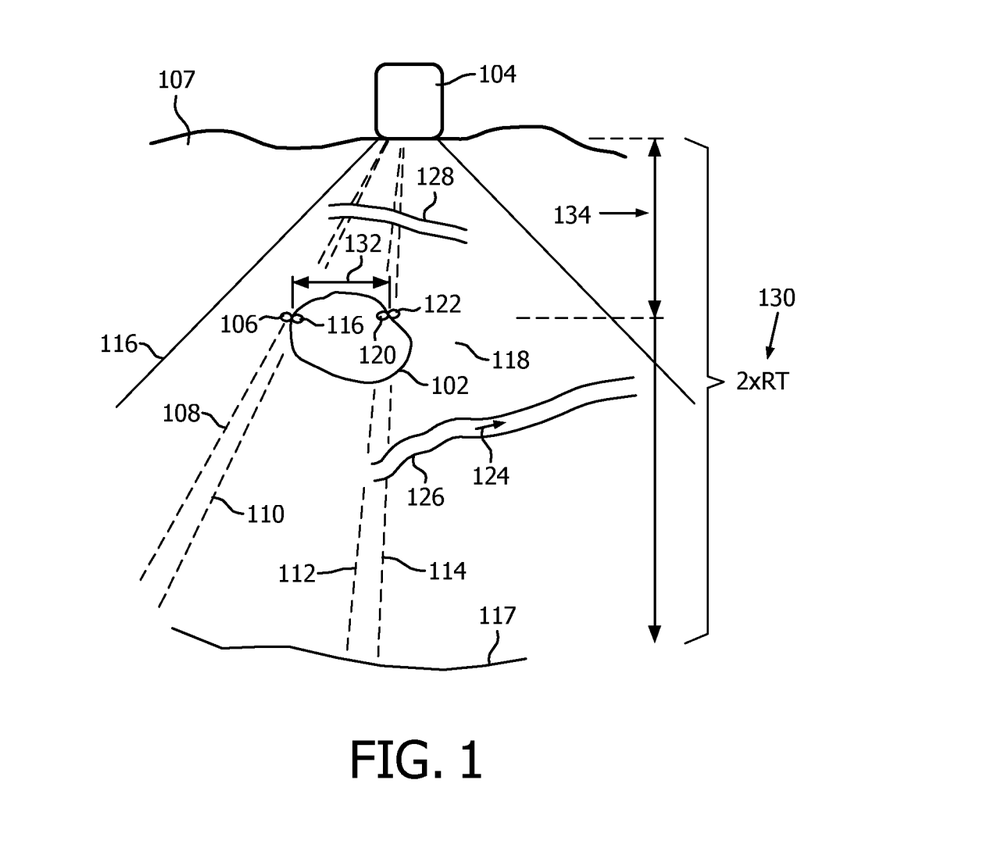
FIG. 1 is a conceptual view of scanning to identify stationary pools, in accordance with the present invention.

FIG. 1 depicts, by way of illustrative and non-limitative example, automatic scanning to identify a stationary pool 102. An acoustic interrogator 104 which includes an ultrasound transducer array and beamforming and other imaging electronics, can be part of a larger device implemented as a medical diagnostic apparatus which includes a video display and a panel having a user controls. An example of such an apparatus that is portable, and therefore suited for point-of-care in for example emergencies, and is small and therefore relatively inexpensive is disclosed in commonly-owned U.S. Pat. No. 7,141,020 to Poland et al. A stationary apparatus with a floor-supported console, for instance, is also within the intended scope of what is proposed herein.

A region 106, within an imaging subject 107, may be a "focal neighborhood", such as a focal zone, or part of the focal zone, of the applied ultrasound including neighboring tissue. The tissue is within the A-line imaging the focal zone, and is the tissue, including tissue deeper and shallower than the focal zone, whose displacement is tracked in connection with a push to the focal zone. The displacement occurs as a result of an acoustic radiation force imaging (ARFI) push whose focus is the focal zone. A number of regions 106 make up an A-line 108 (or any of A-lines 110, 112, 114). The interrogator 104 scans ultrasound to create, on receive, A-lines 108-114 that span a current field-of-view (FOV) 116, i.e., test volume, over the entire sector, in search of one or more stationary pools 102 of blood. The current FOV 116 within the imaging subject 107 may extend entirely through to the contralateral skin surface 117, if imaging is being acquired to that extent in identifying stationary fluid 102. The scan traverses regions 106, 116 in normal tissue 118 and regions 120, 122 within any stationary pool 102 or other lesion that may exist and therefore be identified in the scan. The system, i.e., medical diagnostic apparatus, can discern, based on interrogations to the region 106, 116, 120, 122 (hereinafter "region 106" for short), whether the region contains stationary fluid or not. Acoustic streaming caused by the push to the region 106 allows determination of the fluid or solid character of the region. However, since acoustic streaming could be mistaken for natural flow 124 in an artery 126 or vein 128, that same region 106 is tested for pre-existing motion, i.e., motion pre-existing any push or other ultrasound transmission capable of inducing motion. A pulse train would be capable of inducing motion if it were to have a spatial peak temporal average (SPTA) intensity, i.e., a parameter used in bioeffects measurement, of sufficient strength due to a combination of pulse amplitude, pulse length and pulse repetition frequency (PRF). To a non-motion-inducing pulse train, a push sequence is appended to form a combined sequence. The push sequence may consist of a push pulse, at least one preceding tracking pulse and at least one tracking pulse that follows the push pulse. Accordingly, a first part of the pulse sequence tests for pre-existing motion and the second part tests for solid or fluid. If the region 106 has found to have no pre-existing motion, and to be a fluid, a stationary fluid has been detected. A plurality of clustered regions 106 of stationary fluid is indicative of a pool of stationary fluid, like a pool of blood. The first part of the pulse sequence is closely followed by the second part. In particular, the time period that separates the two parts is less than twice a maximum round-trip time-of-flight 130 in imaging the imaging subject 107 in the course of performing the identifying of stationary fluid. Here, the time period is considered to commence upon completion of most recent pulse of the first part and to end upon commencement of the first pulse of the second part. Alternatively, the second part can be withheld until echoes of the first part are analyzed, and can be foregone for the current region 106 if the analysis reveals natural fluid flow. The scan then proceeds to the next region 106. Therefore, in such an embodiment, the interrogation to distinguish solid from fluid is performable selectively responsive to a result of the interrogation to detect pre-existing movement.

Figure 2:
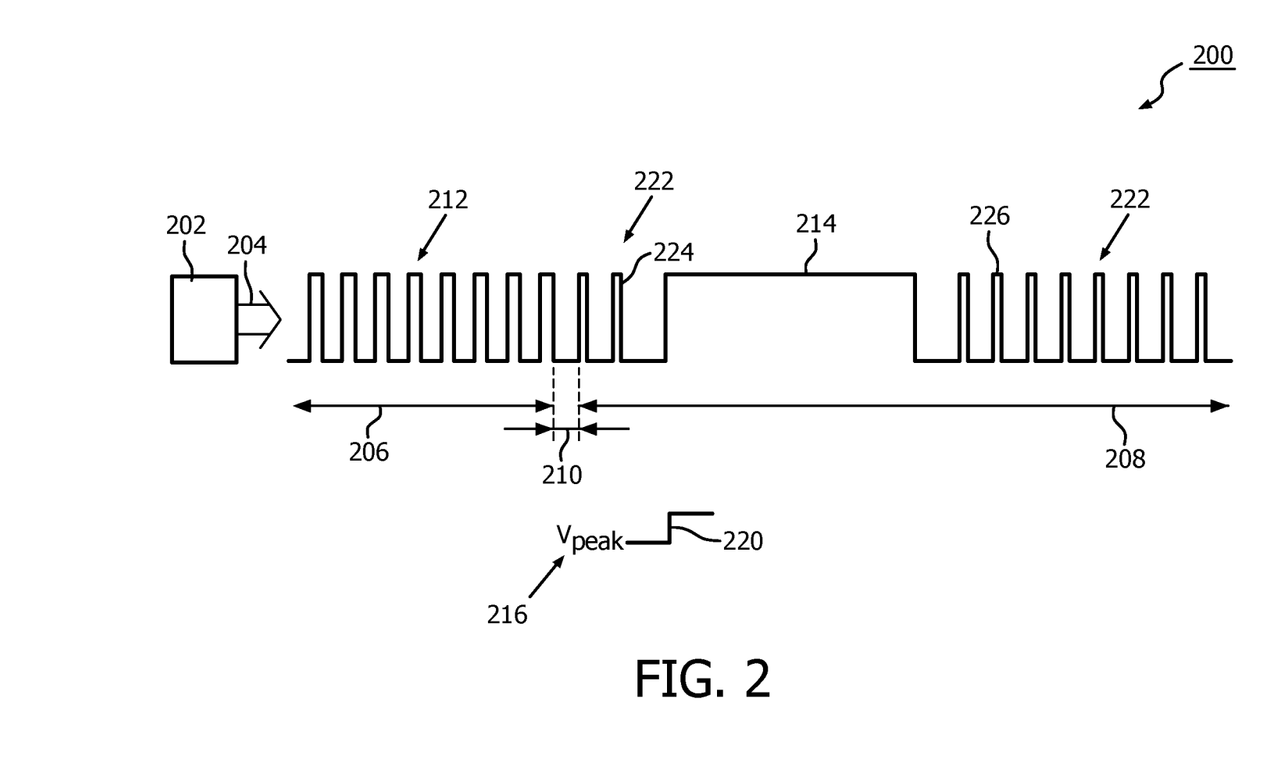
FIG. 2 is a timing diagram of a pulse sequence usable in the scanning, in accordance with the present invention.

FIG. 2 is a timing diagram of an exemplary pulse sequence 200 usable in the scanning. A pulse sequence generator 202 of the acoustic interrogator 104 generates the pulse sequences 200 for transmission 204 to the region 106. A first part 206 and a second part 208 of the sequence 200 are separated by a short time period 210, such that two parts 206, 208 are combined to form a single sequence. The medical diagnostic apparatus does not issue any intervening acoustic pulse transmission 210, i.e., that intervenes between the two parts 206, 208. The pulses, although shown as rectangular, can be sinusoidal or square wave.

The first part 206 consists of pulses, of type I, i.e., blood flow detection pulses 212, that are similar to color flow Doppler pulses and are likewise non-motion-inducing. Displacements and velocities can be obtained using any of the well-known methods such as cross-correlation of successive images to detect a change in round-trip time-of-arrival, which indicates displacement and motion. Methods such as Power Doppler where the total integrated Doppler power is calculated and displayed can be used to aid in the detection of the fluid flow.

Pulse type II, in the second part 208, is a long pulse, referred to as a "push pulse" 214 that is able to cause movement of tissue. The movement is significantly larger for fluids than for solids.

Alternatively, the pulse type II could differ from pulse type I, to likewise achieve the pushing effect, simply by having greater amplitude. Specifically, the peak voltage 216 that is applied in generating a blood flow detection pulse 212 (and perhaps a tracking pulse discussed below) is raised 220 when generating the push pulse 214. Thus, in this alternative embodiment, amplitude is the only parameter that powerwise distinguishes the detection pulse 212 from the push pulse 214 pulse length, for example, is not varied.

Pulse type III is a short pulse for tracking movement of tissue, referred to as a "tracking pulse" 222. It is similar to ultrasound B-mode imaging pulses. Among the tracking pulses 222 of the sequence 200 are one or more preceding pulses 224 and one or more following pulses 226. A tissue image detected via the return echoes of a preceding pulse 224 can serve as a reference against a corresponding image from a following pulse 226, in determining tissue displacement caused by the push pulse 214. Following pulses 226 can also be mutually compared, as demonstrated further below.

Both the pulse type III and the pulse type I can be much shorter in duration than the pulse type II. It is also conceivable that in some embodiments the pulse type I and pulse type III are similar in terms of acoustic parameters such as pulse length and amplitude. In general the amplitude of the three pulses may be different.

Figure 3A:
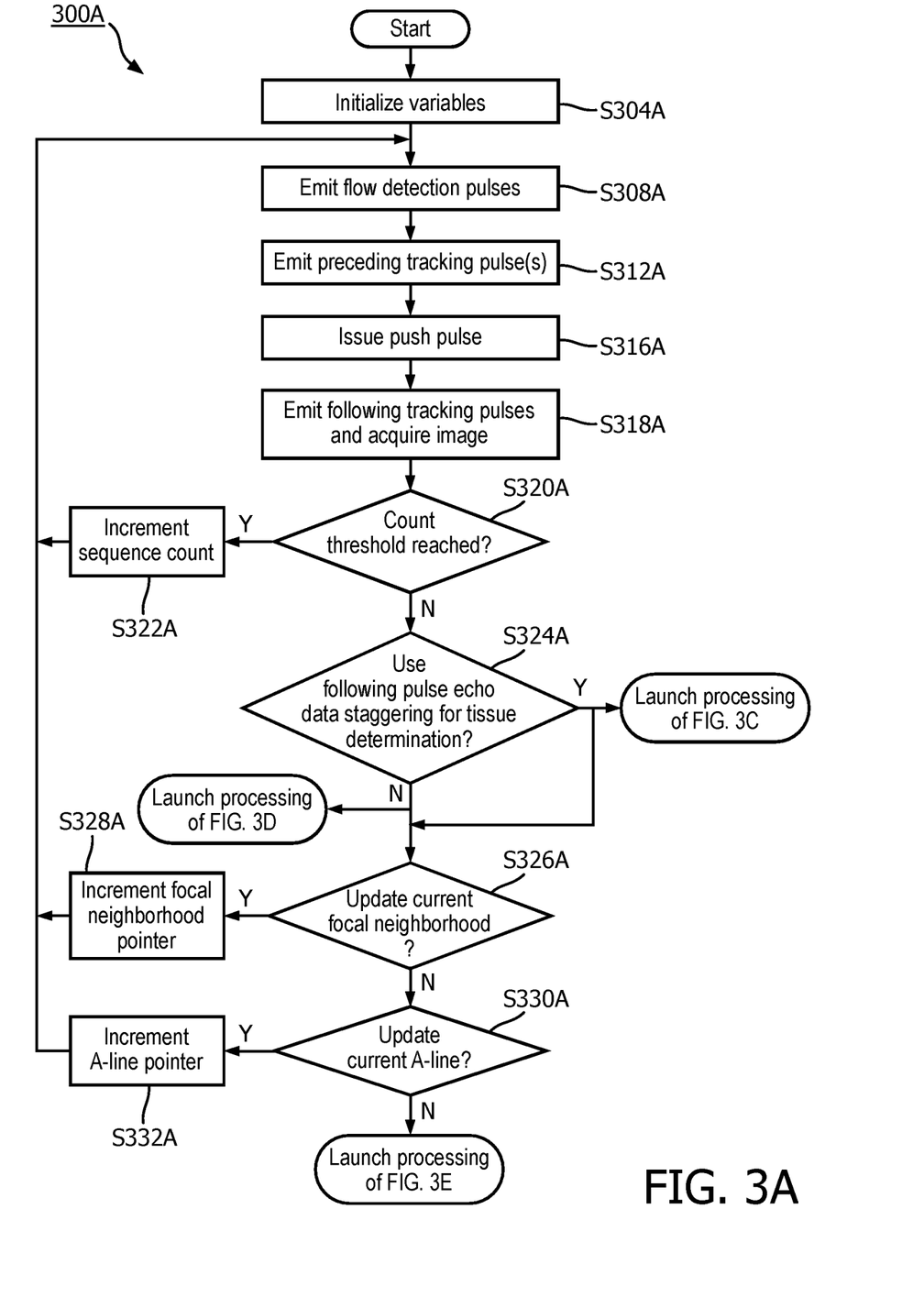
FIGS. 3A-3E are a flow diagram of the scanning and associated processing, in accordance with the present invention.

Operationally, and with reference to FIG. 3A, one or more pools 102 of stationary fluid, if any exist, are dynamically identified through a complete scan spanning the FOV 116, as shown in the exemplary scanning routine 300A. In the example that follows, it is assumed that each detection pulse 212, and each tracking pulse 222, of the sequence 200 is a single pulse; although, each of these pulses may be accompanied by simultaneous pulses laterally distributed in regular spatial intervals, i.e., in parallel. In the latter case, fewer pushes 214 are needed to cover or span the FOV 116.

Figure 3B:
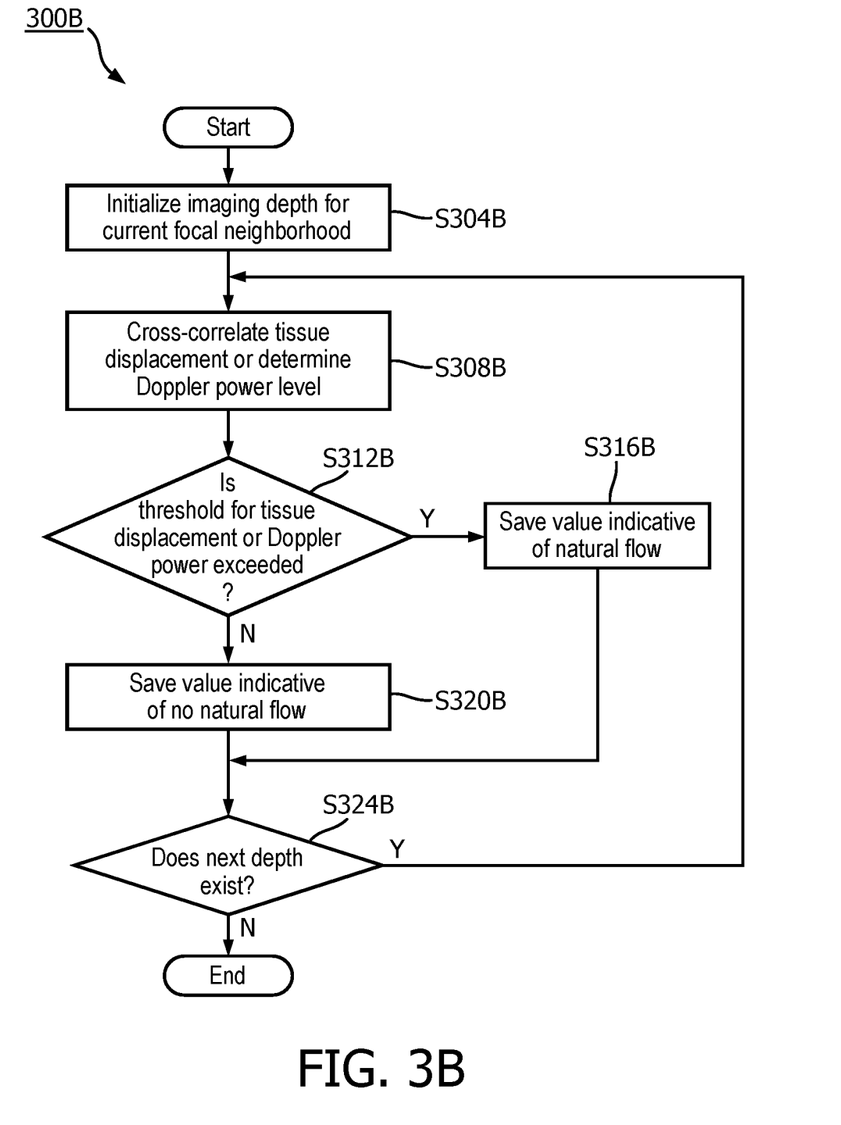
Figure 3C:
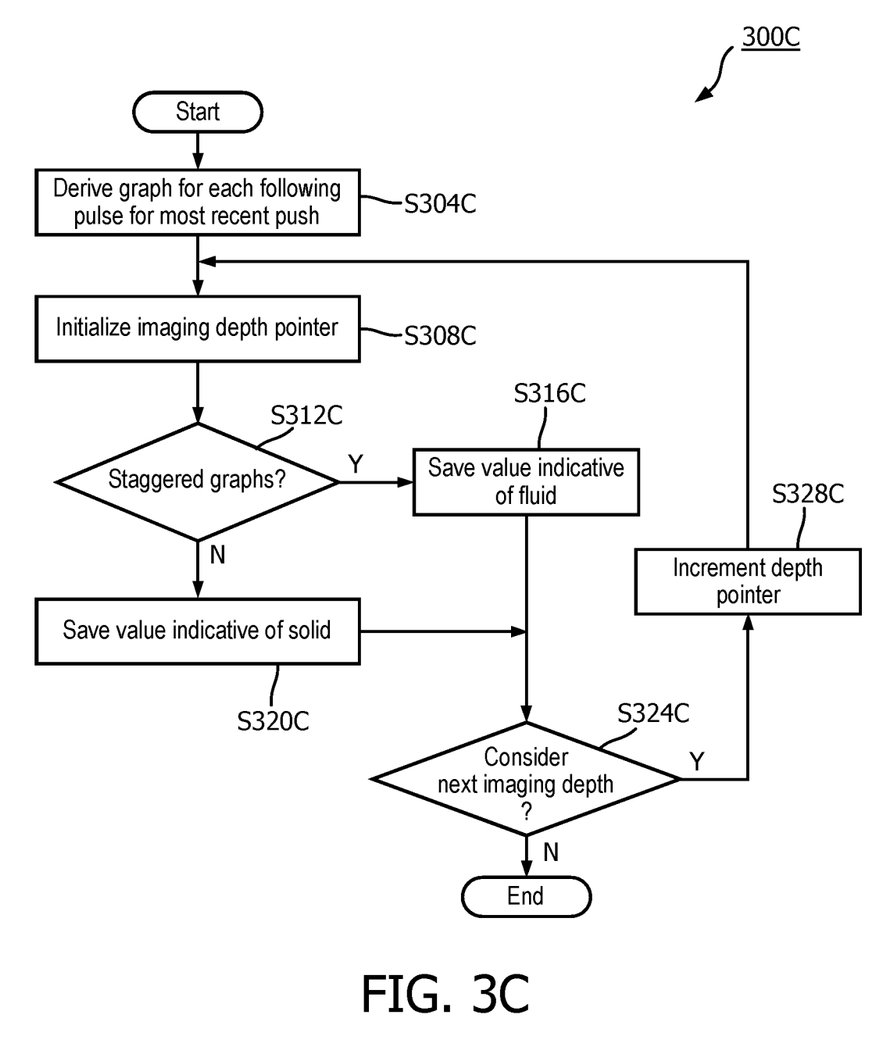
Figure 3D:
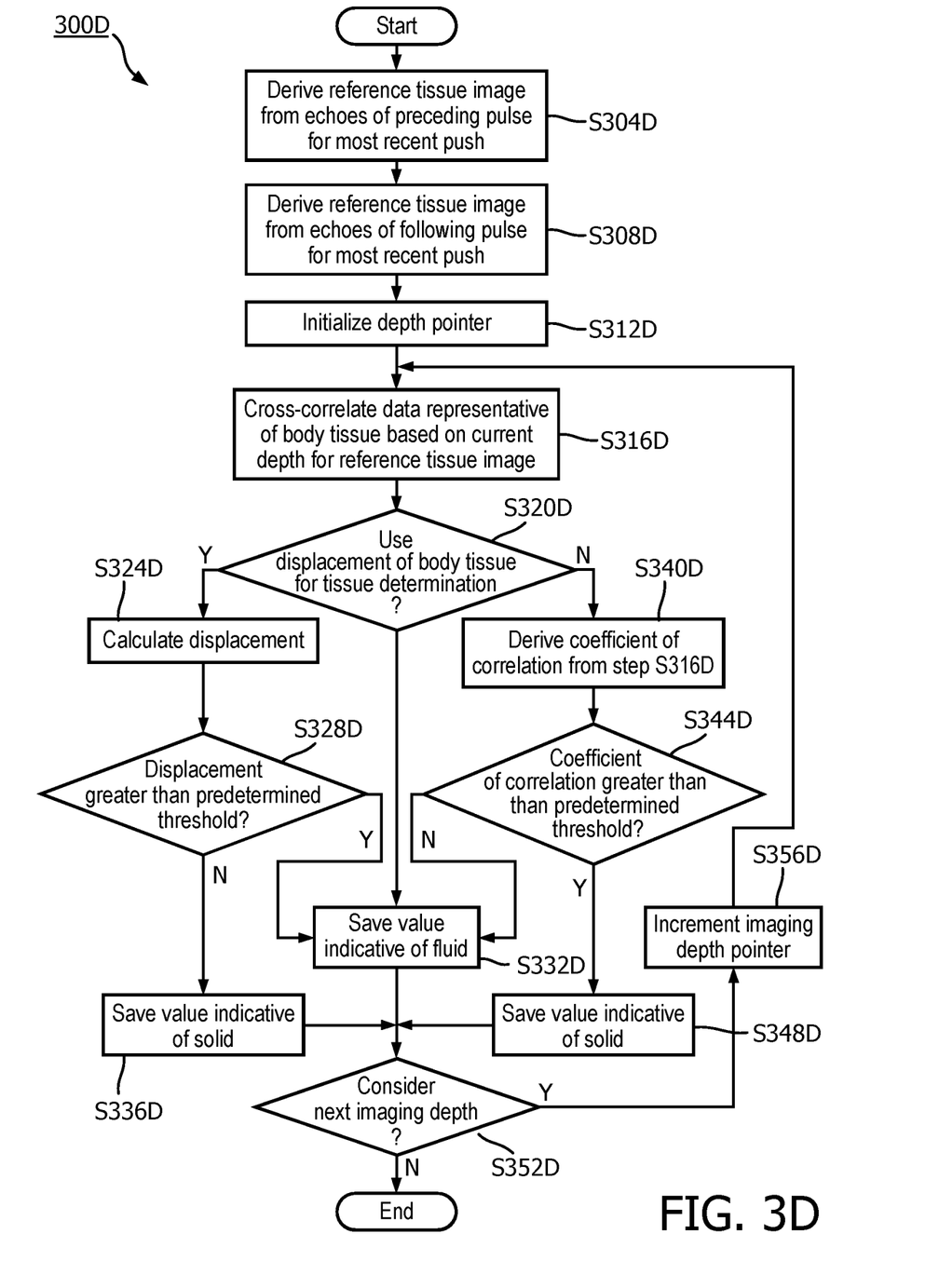
Figure 3E:
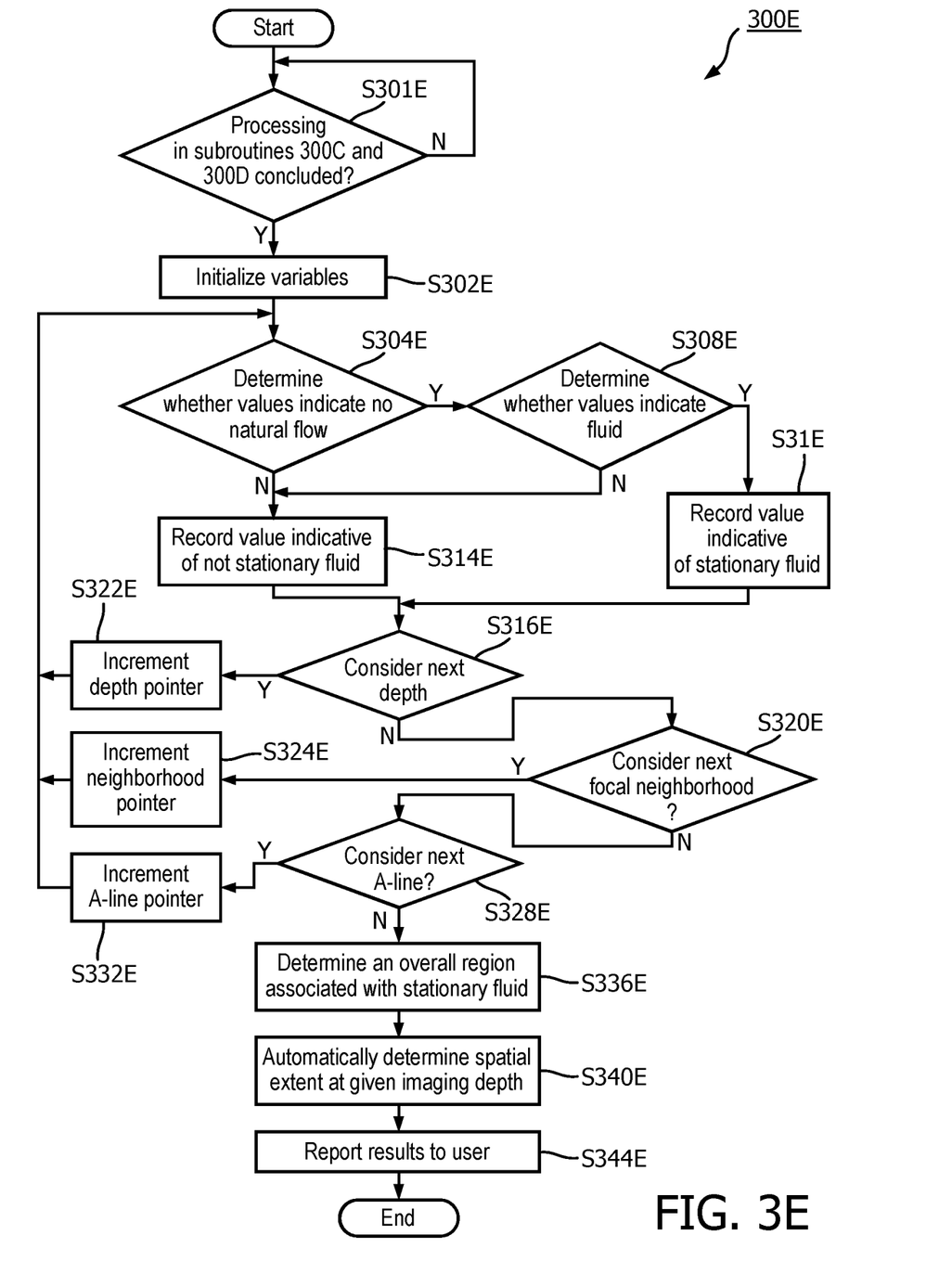

First, the focal neighborhood 106, the A-line 108, a pulse sequence count, a focal neighborhood pointer, and an A-line pointer are initialized in the routine 300 (step S304A). The train of blood flow detection pulses 212 which make up the first part 206 are emitted (step S308A). The acquired imaging is saved. In the case of power Doppler, the imaging from multiple gates at respective imaging depths is acquired and saved. The processing in FIG. 3B is launched to determine the presence or absence of flow by imaging depth, based on the echoes returning from the pulses 212. Next, one or more preceding tracking pulses 224 are emitted, and the acquisition is saved (step S312A). The tracking pulse(s) 224 are immediately followed by the issuance of a push pulse 214 (step S316A). A train of following pulses 226 is then emitted and the imaging is acquired (step S318A). If the pulse sequence count has reached an iteration threshold (step S320A), the sequence count is incremented (step S322A), and return in made to step S308A. Otherwise, if the sequence count has not yet reached the iteration threshold (step S320A), which may be two or more, query is made as to whether distinguishing solid from fluid is to be made based on the staggering of following pulse echo data or based on pre- and post-push tracking (step S324A). If the distinguishing is to be based on following pulse echo data staggering (step S324A), the processing in FIG. 3C is launched. Otherwise, if the distinguishing is to be based on pre- and post-push tracking (step S324A), the processing in FIG. 3D is launched. In either case, if the current focal neighborhood 106 is to be updated (step S326A), the focal neighborhood pointer is incremented (step S328A), and return in made to step S308A. Otherwise, if the current focal neighborhood 106 is not yet to be updated (step S326A), but the current A-line is to be updated (step S330A), the A-line pointer is incremented (step S332A), and return is made to step S308A. If the current A-line is not yet to be updated (S330A), it is time for the end processing, to identify stationary pools 102, which is shown in FIG. 3E which is discussed further below.

Meanwhile, with reference to FIG. 3B, a flow detection subroutine 300B processes the saved echo data from the blood flow detection pulses 212. First, imaging depth is initialized for the current focal neighborhood 106 (step S304B). Then, either tissue displacement is cross-correlated or Doppler power level is determined (step S308B). If the threshold, for tissue displacement or for Doppler power, is exceeded (step S312B), a value is saved indicative of natural flow (step S316B). Otherwise, if the threshold is not exceeded (step S312B), a value is saved indicative of no natural flow (step S320B). If a next depth exists (step S324B), return is made to step S308B.

Also while the scanning routine 300A executes, a staggering detection subroutine 300C, shown in FIG. 3C, for distinguishing between solid and fluid relies on detection as to whether following-pulse echo-data staggering exists. First, a graph is derived for each following pulse 226 for the most recent push 214, i.e., the push in the most recent iteration (step S304C). The graph is of pulse amplitude versus imaging depth. The graph also represents a snapshot in time, i.e., a fixed time after issuance of the respective following pulse 226. An imaging depth pointer is initialized (step S308C). Query is made as to whether, with respect to the current imaging depth, the graphs are staggered (step S312C). Thus, starting from the current imaging depth, the graphs may appear in a depth-wise direction shapes that approximately match each other but are staggered in a depth-wise direction. In this case, the graphs are staggered. Whether or not the graphs are staggered may be determined by cross-correlation. If the graphs are staggered (step S312C), a value is saved indicative of fluid (step S316C). Otherwise, if the graphs are not staggered (step S312C), a value is saved indicative of solid (step S320C). In either case, if a next imaging depth is to be considered (step S324C), the depth pointer is incremented (step S328C), and processing returns to step S312C. Although this subroutine is invoked here after the last push 214 of the series of two or more, it could alternatively or additionally be invoked prior to the last push of the series.

The alternative, or complement, to the staggering detection subroutine 300C is here a pre- and post-push tracking subroutine 300D, shown in FIG. 3D. A depth-wise reference tissue image, or other data that is representative of tissue structure over space and which serves as a reference, is derived from echoes of a preceding pulse 224 for the most recent push 214 (step S304D). A depth-wise tissue image, or other likewise representative data, is also derived from echoes of a following pulse 226 for the most recent push pulse 214 (step S308D). The steps S304D, S308D can be performed in either order. A depth pointer is initialized (step S312D). The two images, or, more generally, the two sets of data that are representative of body tissue, are cross-correlated based on the current depth for the reference tissue image (or reference set) (step S316D). If the determination of solid or liquid is to be made based on the push-induced total non-spatially-overlapping displacement of body tissue (step S320D), the displacement is calculated (step S324D). The push-induced total non-spatially-overlapping displacement of body tissue, with respect to a preceding tracking pulse, i.e., a tracking pulse that precedes the push(es), and a following tracking pulse which is a tracking pulse that follows the push(es), is herein defined as the displacement in body tissue in the push direction, i.e., a one-way direction, as a result of the push(es) and as measured from echo data of the preceding and following pulses. If the displacement is greater than a predetermined threshold (step S328D), a value is saved indicative of fluid (step S332D). Otherwise, if the displacement is less than or equal to the threshold (step S328D), a value is saved indicative of solid (step S336D). On the other hand, if the determination of solid or liquid is not to be made based on the push-induced total non-spatially-overlapping displacement (step S320D), a coefficient of correlation is derived from step S316D (step S340D). If the coefficient of correlation is less than or equal to a predetermined threshold (step S344D), a value is saved indicative of fluid (step S332D). Otherwise, if the coefficient of correlation is greater than a predetermined threshold (S344D), a value is saved indicative of solid (step S348D). In any event, if a next imaging depth is to be considered (step S352D), the imaging depth pointer is incremented (step S356D), and processing returns to step S316. The pre- and post-push tracking subroutine 300D optionally can be repeated for a different following pulse 226, to verify the above determinations.

Continuing with the scanning routine 300A and specifically its end processing subroutine 300E, reference is now made to FIG. 3E. When processing concludes in the subroutines 300C, 300D (step S301E), the A-line pointer, focal neighborhood pointer, an imaging depth pointer are initialized (step S302E). If at the current depth in the current focal neighborhood, the values indicate no natural flow (step S304E) and fluid (step S308E), a value indicative of stationary fluid is recorded (step S312E). Otherwise, if the values indicate natural flow (step S304E), or no natural flow (step S304E) but solid (step S308E), a value of not stationary fluid is recorded (step S314E). If a next depth is to be considered (step S316E), the depth pointer is incremented (step S322E), and return is made to step S304E. Otherwise, if a next depth is not to be considered (step S316E), query is made as to whether a next focal neighborhood 106 is to be considered (step S320E). If a next focal neighborhood 106 is to be considered (step S320E), the neighborhood pointer is incremented (step S324E), and return is made to step S304E. If, on the other hand, a next focal neighborhood 106 is not to be considered (step S320E), query is made as to whether a next A-line is to be considered (step S328E). If a next A-line is to be considered (step S328E), the A-line pointer is incremented (step S332E), and return is made to step S304E. If, however, a next A-line is not to be considered (step S328E), cluster analysis is used to find an overall region made up of one or more regions determined to have stationary fluid (step S336E). A clustering criterion can be based on, for example, Mahalanobis distance. A spatial extent 132 at, for instance, a given imaging depth 134 is automatically determined (step S340E). The entire blood pool 102 can likewise be delimited. The results are reported to the user (step S344E). An example would be an on-screen color-coded image to denote pools 102 of stationary fluid.

The entire scanning routine 300A set forth above is executable by the medical diagnostic imaging apparatus automatically and without the need for user intervention, although the user can manually or automatically move the current FOV 116 of the apparatus in further search of stationary fluid.

Dynamically identifying a stationary body of fluid within a test volume by scanning within the volume can entail using a first part of a pulse sequence to acoustically interrogate a region within the volume to detect pre-existing movement and, via a separate acoustic interrogation constituting the second part of the pulse sequence, acoustically interrogating the region to distinguish solid from fluid. The scanning is with both interrogations as a unit, so as to span the volume with the interrogations. The body is identified, dynamically based on an outcome of the interrogations. The scanning may span, for the identifying, a current field of view, including normal tissue, within an imaging subject. The procedure, from scanning to identifying, may be performed automatically and without need for user intervention, although the user can optionally change the field of view to further search for stationary fluid.

While the invention has been illustrated and described in detail in the drawings and foregoing description, such illustration and description are to be considered illustrative or exemplary and not restrictive; the invention is not limited to the disclosed embodiments.

For example, blood may be distinguished from solid tissue according to a measured acoustic velocity.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. An acoustic interrogation system for identifying a stationary body of fluid within a test volume, the system comprising:
an ultrasound transducer array; and
a processor circuit coupled to the ultrasound transducer array and configured to cause the ultrasound transducer array to transmit ultrasound pulses according to a single sequence comprised of at least a first part and a second part, the single sequence configured for identifying the stationary body of fluid within the test volume,
wherein the first part of the single sequence comprises a first plurality of pulses configured to detect motion within a region of the test volume without inducing motion in the region,
wherein the second part of the single sequence comprises at least one motion-inducing pulse appended to the first part, at least one first tracking pulse preceding the at least one motion-inducing pulse and at least one second tracking pulse following the at least one motion-inducing pulse,
wherein the processor circuit is configured to:
determine whether fluid flow is present within the region based on echoes detected by the ultrasound transducer array in response to the first plurality of ultrasound pulses,
analyze echoes responsive to the at least one first tracking pulse and the at least one second tracking pulse associated with the second part to determine whether the region corresponds to a fluid or a solid, wherein the analysis comprises generating graphs of pulse amplitude versus imaging depth and determining whether the graphs are staggered in a depth-wise direction, wherein graphs staggered in the depth-wise direction are indicative of the fluid, and
determine that the region corresponds to stationary fluid based on the determination that fluid flow is not present and the determination that the region corresponds to the fluid.

2. The system of claim 1,
wherein the single sequence consists of the first part and the second part,
wherein the system is configured to issue pulses in accordance with the single sequence without issuing an acoustic pulse transmission that intervenes between said first and second parts.

3. The system of claim 1,
wherein the region is a first region of a plurality of regions within the test volume and with a field of view of the ultrasound transducer array,
wherein the processor circuit is configured to cause the ultrasound transducer array to transmit pulses in accordance with a plurality of single sequences for determining a spatial extent of the stationary body of fluid within the test volume.

4. The system of claim 3,
wherein the processor circuit is configured to cause the ultrasound transducer array to transmit a sequence of pulses in accordance with a first plurality of two-part sequences toward the first region,
wherein the sequence of pulses includes a tracking pulse that precedes and a tracking pulse that follows at least two intervening motion-inducing pulses.

5. The system of claim 1, wherein the second part further comprises a first plurality of tracking pulses that precede and a second plurality of tracking pulses that follow the motion-inducing pulse.

6. The system of claim 1,
wherein the first part comprises a blood flow detection pulse,
wherein the second part comprises an acoustic-radiation-force-imaging push pulse, wherein amplitude is the only parameter that power-wise distinguishes the blood flow detection pulse from the acoustic-radiation-force-imaging push pulse.

7. The system of claim 1, wherein pulses of the first part of the single sequence are configured for identifying fluid within the test volume that is already moving prior to transmission of the pulses of the first part.

8. The system of claim 1, said test volume comprising a plurality of regions, said region being among said plurality of regions, said scanning comprising, after performing said both interrogations of said region, performing said both interrogations of a next region of said test volume.

9. The system of claim 1, wherein the processor circuit is configured to determine differences in tissue, at least in part, by computing a correlation coefficient between successive images representative of the tissue.

10. The system of claim 9, wherein the processor circuit is further configured, based on the computed correlation coefficient, to dynamically determining a spatial extent of a stationary body of fluid.

11. The system of claim 1,
wherein determining whether the region corresponds to the fluid or the solid is further based on cross-correlating an imaging-depth-wise reference tissue image based on echoes generated responsive to the at least one first tracking pulse and an imaging-depth-wise tissue image based on echoes generated responsive to the at least one second tracking pulse.

12. The system of claim 1, wherein individual pulses of the first plurality of pulses are shorter in length than the motion-inducing pulse.

13. The system of claim 1, wherein individual pulses of the first plurality of pulses have a same length as the motion-inducing pulse.

* * * * *